US012742150B2

(12) United States Patent
Zhao et al.

(10) Patent No.: US 12,742,150 B2
(45) **Date of Patent: *Sep. 22, 2026**

(54) METHOD FOR PRESERVING FERMENTATION BROTH OF ENGINEERED STRAIN OF D-PSICOSE-3-EPIMERASE

(71) Applicant: HENAN ZHONGDA HENGYUAN BIOTECHNOLOGY STOCK CO., LTD., Luohe City (CN)

(72) Inventors: Zhewei Zhao, Luohe City (CN); Sanying Wang, Luohe City (CN); Ziheng Jin, Luohe City (CN); Yanjun Wen, Luohe City (CN); Linzheng Li, Luohe City (CN); Rongrong Xie, Luohe City (CN); Tianyi Pan, Luohe City (CN)

(73) Assignee: HENAN ZHONGDA HENGYUAN BIOTECHNOLOGY STOCK CO., LTD., Luohe City (CN)

( * ) Notice: Subject to any disclaimer, the term of this patent is extended or adjusted under 35 U.S.C. 154(b) by 451 days.

This patent is subject to a terminal disclaimer.

(21) Appl. No.: 18/370,469

(22) Filed: Sep. 20, 2023

(65) Prior Publication Data

US 2024/0301344 A1 Sep. 12, 2024

(30) Foreign Application Priority Data

Mar. 8, 2023 (CN) ......................... 202310215892.6

(51) Int. Cl.
*C12N 1/205* (2026.01)
*C12N 9/36* (2006.01)
*C12N 9/90* (2006.01)

(52) U.S. Cl.
CPC ........... *C12N 1/205* (2021.05); *C12N 9/2462* (2013.01); *C12N 9/90* (2013.01); *C12N 2500/12* (2013.01); *C12N 2501/73* (2013.01); *C12Y 501/03* (2013.01)

(58) Field of Classification Search
None
See application file for complete search history.

(56) References Cited

U.S. PATENT DOCUMENTS 12,012,627 B2 * 6/2024 Wang ...................... C12P 19/24
2011/0269189 A1 * 11/2011 Wang ................. C08B 37/0003
435/72

FOREIGN PATENT DOCUMENTS

CN 112852795 A * 5/2021 ............. C12N 15/70
CN 113957064 A * 1/2022 ........... C12Y 501/03

OTHER PUBLICATIONS

Suphantharika et al. Bioprocess Engineering 12: 181-186, 1995 (Year: 1995).*

* cited by examiner

*Primary Examiner* — Christian L Fronda

(57) ABSTRACT

A method for preserving a fermentation broth of an engineered strain of D-psicose-3-epimerase includes: adding a lysozyme into a fermentation broth of an engineered strain of D-psicose-3-epimerase, stirring to make the OD600 of the fermentation broth less than or equal to 1 to obtain an enzyme solution; and adjusting the enzyme solution to be weakly alkaline with an alkali liquor, and storing the weakly alkaline enzyme solution at room temperature. According to the invention, the enzyme solution is obtained by adding the lysozyme after fermentation, and then adjusted to be weakly alkaline. The lysozyme can dissolve the engineered strain to release the enzyme, and can also inhibit the growth of microorganisms. The alkaline environment of the enzyme solution can further inhibit the growth of other microorganisms in the enzyme solution. Therefore, the storage life of the enzyme solution is prolonged while ensuring the enzyme activity.

1 Claim, No Drawings

METHOD FOR PRESERVING FERMENTATION BROTH OF ENGINEERED STRAIN OF D-PSICOSE-3-EPIMERASE

This application claims priority to Chinese Patent Application No. 202310215892.6, filed on Mar. 8, 2023, which is incorporated by reference for all purposes as if fully set forth herein.

FIELD OF THE INVENTION

The invention relates to the field of bioengineering, and specifically to a method for preserving a fermentation broth of an engineered strain of D-psicose-3-epimerase.

DESCRIPTION OF THE RELATED ART

D-psicose is a rare sugar, which is an epimer of D-fructose. It yields 70% of the sweetness of sucrose and only 0.3% of the metabolic energy of sucrose, and therefore is a good substitute for sucrose. Studies have shown that D-psicose can also reduce the absorption of fructose and glucose in the body, and reduce the accumulation of fat, thereby reducing the risk of type 2 diabetes and obesity. At present, D-psicose has a wide application prospect in foods and health care products.

The industrial production of D-psicose is mainly based on a biological enzymatic method, i.e., using fructose as a substrate and using D-psicose-3-epimerase to catalyze the conversion of fructose to D-psicose. D-psicose-3-epimerase is mostly obtained by large-scale fermentation and culture of constructed engineered strains. The release of the enzyme in the D-psicose-3-epimerase fermentation broth and the storage of the enzyme solution are very important for the industrial production of D-psicose.

Conventional processes for treating and preserving the D-psicose-3-epimerase fermentation broth involve centrifugation, redissolution, homogenization at low temperature, secondary centrifugation, followed by storage at low temperature (generally 4° C.). However, as the storage time increases, D-psicose-3-epimerase will be seriously inactivated. In addition, after 15 days of low-temperature storage, the enzyme solution begins to stink (indicating a decrease in the enzyme activity), leading to increased D-psicose production costs of enterprises.

At present, there are also reports on improving the storage effect and ensuring the enzyme activity of the enzyme solution of D-psicose-3-epimerase. For example, CN115074350A discloses a method for reducing enzyme activity loss of D-psicose-3-epimerase liquid. In this method, $MgSO_4$ or $Na_2CO_3$ is added into the supernatant (i.e., enzyme solution) obtained after secondary centrifugation, and the resultant solution is stored at low temperature (i.e., 4° C.). Although this method prolongs the storage life of the enzyme solution to a certain extent, complex steps are required for treating the fermentation broth, the enzyme solution may stink (indicating a decrease in the enzyme activity) during storage, and the enzyme solution needs to be stored at a low temperature of 4° C. Consequently, enterprises need to provide a large number of freezers to store the large amount of enzyme solution obtained by large-scale culture is often large, leading to high power consumption in the storage process.

Based on the above, how to solve the problems of complex steps required for treating the D-psicose-3-epimerase fermentation broth and high storage costs of the enzyme solution is of great significance to the industrial production of D-psicose.

SUMMARY OF THE INVENTION

Accordingly, the invention provides a method for preserving a fermentation broth of an engineered strain of D-psicose-3-epimerase. The method features simple treatment steps and can realize the long-term storage of the enzyme solution of D-psicose-3-epimerase at room temperature while ensuring the enzyme activity during storage, thereby reducing the storage costs of the enzyme solution and the production costs of D-psicose.

To achieve the above objective, the following technical solutions are adopted in the invention.

The method for preserving a fermentation broth of an engineered strain of D-psicose-3-epimerase according to the invention includes: adding a lysozyme into a fermentation broth of an engineered strain of D-psicose-3-epimerase, stirring to make the OD600 of the fermentation broth less than or equal to 1 to obtain an enzyme solution; and adjusting the enzyme solution to be weakly alkaline with an alkali liquor, and storing the weakly alkaline enzyme solution at room temperature.

In the invention, the enzyme solution is obtained by adding the lysozyme after fermentation of the engineered strain, and then the enzyme solution is adjusted to be weakly alkaline. The weakly alkaline enzyme solution can be stored at room temperature for a long time, with a storage life of 60 days or more. The method is simple and reliable, and simplifies the steps required for treating the fermentation broth of the engineered strain.

In the invention, the lysozyme added into the fermentation broth dissolves the fermented engineered strain to release D-psicose-3-epimerase in the cells of the engineered strain. In addition, during storage, the lysozyme can prevent the protease secreted by the surviving engineered strain from degrading D-psicose-3-epimerase, and can also inhibit the protease secreted by the growth of other microorganisms from degrading D-psicose-3-epimerase.

In the invention, because the obtained enzyme solution is stored at room temperature under a weak alkaline condition, the growth of microorganisms in the enzyme solution is inhibited to avoid as much as possible the stinking of the enzyme solution and a serious enzyme activity loss during storage. In addition, storage at room temperature does not require the use of low-temperature storage equipment such as freezers, which not only reduces the consumption of freezers, but also reduces power consumption.

In a preferred implementation of the invention, the concentration of the lysozyme is greater than or equal to 0.06 g/L. In other words, at least 0.06 g of the lysozyme is added per liter of the fermentation broth, so that the fermented engineered strain can be dissolved as much as possible.

In a more preferred implementation of the invention, the concentration of the lysozyme is 0.06 g/L to 0.2 g/L. In other words, the amount of the lysozyme per liter of the fermentation broth is preferably 0.06 g to 0.2 g. More preferably, the concentration of the lysozyme is 0.1 g/L.

In a preferred implementation of the invention, in the step of adjusting the enzyme solution to be weakly alkaline with an alkali liquor, the alkali liquor is a sodium hydroxide solution, a potassium hydroxide solution, a disodium hydrogen phosphate solution, or a disodium hydrogen phosphate solution; and the pH of the enzyme solution after the adjustment with the alkali liquor is 7.5 to 8.5. In the invention, the pH of the enzyme solution may be adjusted with either a strong alkaline solution (such as a sodium hydroxide solution commonly used in experiments) or a weak alkaline solution such as a disodium hydrogen phosphate solution or a dipotassium hydrogen phosphate solution. In other words, the alkali liquor may be flexibly selected according to actual situations. In addition, in the invention, the adjustment of the pH of the enzyme solution to 7.5 to 8.5 effectively inhibits the growth of microorganisms in the enzyme solution, thereby avoiding the stinking of the enzyme solution and a serious enzyme activity loss during storage. More preferably, the alkali liquor is a sodium hydroxide solution, and the pH of the enzyme solution after the adjustment with the alkali liquor is 8.0.

In a preferred implementation of the invention, in the step of storing the weakly alkaline enzyme solution at room temperature, the room temperature is lower than or equal to 30° C. In spring and autumn, the room temperature is generally 20° C. In winter, the room temperature is generally 10° C. or below. In summer, the room temperature is generally 30° C. or below. The preservation method of the invention can realize the storage of the fermentation broth of the engineered strain of D-psicose-3-epimerase at room temperature in all seasons of the year, can ensure the enzyme activity of the enzyme solution and avoid the stinking of the enzyme solution, and can reduce the power consumption, thereby reducing the costs of industrial production of D-psicose. Therefore, the popularization of the invention is of important significance for D-psicose production enterprises.

Compared with conventional schemes (i.e., centrifugation+homogenization+centrifugation+storage at 4° C.), the invention has the following advantages.

In the invention, the enzyme solution is obtained by adding the lysozyme at a certain ratio after the fermentation of the engineered strain, and then the enzyme solution is adjusted to be weakly alkaline and stored at room temperature for a long time. The invention omits the centrifugation, secondary centrifugation, and high-pressure homogenization steps in conventional schemes, making the treatment and preservation of the fermentation broth simpler and more convenient. The enzyme solution treated by the invention can be stored at room temperature for 60 days or more without becoming stinky, and the enzyme activity loss after 60 days of storage at room temperature can be controlled to be 15% or less (after 60 days of storage at room temperature in winter, the enzyme activity of the enzyme solution basically has no loss), which meets the requirements for the industrial production of D-psicose in enterprises.

In the invention, the lysozyme added into the fermentation broth dissolves the fermented engineered strain to release D-psicose-3-epimerase in the cells of the engineered strain. In addition, during storage, the lysozyme can prevent the protease secreted by the surviving engineered strain from degrading D-psicose-3-epimerase, and can also inhibit the protease secreted by the growth of other microorganisms from degrading D-psicose-3-epimerase.

In the invention, because the obtained enzyme solution is stored at room temperature under a weak alkaline condition, the growth of microorganisms in the enzyme solution is inhibited to avoid as much as possible the stinking of the enzyme solution and a serious enzyme activity loss during storage. In addition, storage at room temperature does not require the use of low-temperature storage equipment such as freezers, which not only reduces the consumption of freezers, but also reduces power consumption.

Taking the storage of 4000 liters of the enzyme solution as an example, the conventional 4° C. storage condition requires 20 freezers with a capacity of 300 L to store 4000 liters of the enzyme solution. Assuming that the daily power consumption of each freezer is 1 kWh, the total power consumption required for storage at the low temperature for 60 days is 1200 kWh. Assuming that the freezers run for 300 days a year, the total annual power consumption is 36000 kWh. The invention allows for the storage at room temperature all the year round and does not require the use of any freezer. In this way, the equipment investments of at least 20 freezers are saved, and a remarkable power-saving effect is achieved (at least 36000 kWh of electricity can be saved every year), thereby reducing the production costs of enterprises. The popularization of the invention is of important significance.

DETAILED DESCRIPTION OF THE PREFERRED EMBODIMENTS

The invention will be described in detail below through specific examples. Any equipment used in the invention is routine laboratory equipment unless otherwise particularly indicated. Any reagent used in the invention is a commonly used experimental reagent unless otherwise particularly indicated.

It should be noted that in the examples of the invention, the enzyme activity is determined by the following method: using 1 wt % fructose solution (formulated by a pH 8.0 potassium phosphate buffer containing 1 mM $Mn^{2+}$) as a base liquid, adding an enzyme solution at an appropriate ratio, and reacting at 60° C. for 10 min; after the reaction, treating in a boiling water bath for 5 min; determining the content of D-psicose by high-performance liquid chromatography (HPLC); and determining the enzyme activity of the enzyme solution of D-psicose-3-epimerase through calculation according to the determined D-psicose content and the reaction time (i.e., 10 min). The enzyme activity in the invention is defined as the number of units (U) per ml. One unit (U) of enzyme activity is 1 μmol of D-psicose produced per minute at pH 8.0 and 60° C.

It should be noted that the engineered strain of D-psicose-3-epimerase mentioned in the examples of the invention is a recombinant *Bacillus subtilis* engineered strain B-3-1 (which has been disclosed in Chinese Patent Application No. CN202010496928.9 entitled "Psicose 3-epimerase mutant, engineered strain for expressing same and application thereof"). It should also be noted that the fermentation broth of the engineered strain of D-psicose-3-epimerase used in the examples of the invention is obtained through fermentation with the following steps.

Step S1: Formulation of culture medium (including a seed medium, a fermentation medium, and a feed medium)

Seed medium: Peptone 10 g/L, yeast powder 5 g/L, and sodium chloride 10 g/L, sterilized at 121° C. for 20 min, followed by the addition of kanamycin to 50 mg/L under aseptic conditions.

Fermentation medium: Peptone 10 g/L, yeast powder 5 g/L, potassium dihydrogen phosphate 2.5 g/L, dipotassium hydrogen phosphate 15 g/L, manganese chloride tetrahydrate 0.1 g/L, and glucose 6 g/L, sterilized at 121° C. for 20 min.

Feed medium: 50 wt % glucose, sterilized at 121° C. for 20 min.

Step S2: A seed culture of the engineered strain of D-psicose-3-epimerase is obtained using the seed medium.

The recombinant *Bacillus subtilis* engineered strain B-3-1 is inoculated into the seed medium and cultured at 37° C. at 200 rpm for 14 h to obtain the seed culture of the engineered strain of D-psicose-3-epimerase.

Step S3: The seed culture is fermented and cultured to obtain a fermentation broth of the engineered strain of D-psicose-3-epimerase.

The seed culture is inoculated in the fermentation medium according to a volume ratio of 0.1% (i.e., 0.1% ml of the seed culture is inoculated per ml of the fermentation medium) for fermentation and culture. Conditions of fermentation and culture include: a fermentation temperature of 37° C.; an initial stirring speed of 200 rpm; and an aeration rate of 1 vvm. The stirring speed is adjusted according to the dissolved oxygen in the fermentation process so that the dissolved oxygen is always 10% or higher. In the fermentation process, the feed medium is added in a fed-batch mode, and the OD600 value is detected for samples. When the OD600 value no longer increases, it is considered that the fermentation is complete, and the fermentation broth of the engineered strain of D-psicose-3-epimerase is obtained.

Example 1

After the fermentation of the engineered strain of D-psicose-3-epimerase was complete (i.e., the OD600 value of the fermentation broth no longer increases), aeration was stopped, and the lysozyme was added in an amount of 0.1 g/L (i.e., the concentration of the lysozyme in the fermentation broth is 0.1 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the enzyme solution was adjusted to pH 8.0 with a NaOH solution, and stored at 20° C. (room temperature in spring and autumn). Samples were taken every 10 days. The enzyme activity of each sample was determined.

Example 2

After the fermentation of the engineered strain of D-psicose-3-epimerase was complete (i.e., the OD600 value of the fermentation broth no longer increases), aeration was stopped, and the lysozyme was added in an amount of 0.1 g/L (i.e., the concentration of the lysozyme in the fermentation broth is 0.1 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the enzyme solution was adjusted to pH 8.0 with a NaOH solution, and stored at 30° C. (room temperature in summer). Samples were taken every 10 days. The enzyme activity of each sample was determined.

Example 3

After the fermentation of the engineered strain of D-psicose-3-epimerase was complete (i.e., the OD600 value of the fermentation broth no longer increases), aeration was stopped, and the lysozyme was added in an amount of 0.1 g/L (i.e., the concentration of the lysozyme in the fermentation broth is 0.1 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the enzyme solution was adjusted to pH 8.0 with a NaOH solution, and stored at 10° C. (room temperature in winter). Samples were taken every 10 days. The enzyme activity of each sample was determined.

Example 4

After the fermentation of the engineered strain of D-psicose-3-epimerase was complete (i.e., the OD600 value of the fermentation broth no longer increases), aeration was stopped, and the lysozyme was added in an amount of 0.06 g/L (i.e., the concentration of the lysozyme in the fermentation broth is 0.06 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the enzyme solution was adjusted to pH 8.0 with a NaOH solution, and stored at 30° C. (room temperature in summer). Samples were taken every 10 days. The enzyme activity of each sample was determined.

Example 5

After the fermentation of the engineered strain of D-psicose-3-epimerase was complete (i.e., the OD600 value of the fermentation broth no longer increases), aeration was stopped, and the lysozyme was added in an amount of 0.15 g/L (i.e., the concentration of the lysozyme in the fermentation broth is 0.15 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the enzyme solution was adjusted to pH 8.0 with a NaOH solution, and stored at 30° C. (room temperature in summer). Samples were taken every 10 days. The enzyme activity of each sample was determined.

Example 6

After the fermentation of the engineered strain of D-psicose-3-epimerase was complete (i.e., the OD600 value of the fermentation broth no longer increases), aeration was stopped, and the lysozyme was added in an amount of 0.1 g/L (i.e., the concentration of the lysozyme in the fermentation broth is 0.1 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the pH of the enzyme solution was adjusted to 7.5 with a NaOH solution, and stored at 30° C. (room temperature in summer). Samples were taken every 10 days. The enzyme activity of each sample was determined.

Example 7

After the fermentation of the engineered strain of D-psicose-3-epimerase was complete (i.e., the OD600 value of the fermentation broth no longer increases), aeration was stopped, and the lysozyme was added in an amount of 0.1 g/L (i.e., the concentration of the lysozyme in the fermentation broth is 0.1 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the enzyme solution was adjusted to pH 8.5 with a NaOH solution, and stored at 30° C. (room temperature in summer). Samples were taken every 10 days. The enzyme activity of each sample was determined.

Comparative Example 1

After the fermentation of the engineered strain of D-psicose-3-epimerase was complete (i.e., the OD600 value of the fermentation broth no longer increases), aeration was stopped, and the lysozyme was added in an amount of 0.1 g/L (i.e., the concentration of the lysozyme in the fermentation broth is 0.1 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the enzyme solution was adjusted to pH 8.0 with a NaOH solution, and stored at 4° C. Samples were taken every 10 days. The enzyme activity of each sample was determined.

Comparative Example 2: Centrifugation+Redissolution+Homogenization+Storage at 4° C.

The fermentation broth of the engineered strain of D-psicose-3-epimerase was centrifuged at 5000 rpm for 30 min, and the supernatant was removed to obtain fermented cells. The fermented cells were re-dissolved in pH 8.0 potassium phosphate buffer to an equal volume (i.e., the volume after redissolution was equal to that of the original fermentation broth of D-psicose-3-epimerase). Then, the resultant solution was homogenized with a homogenizer to release intracellular cells. The homogenizer operated at a temperature of 4° C. and a pressure of 800 bar. After homogenization, the solution was centrifuged at 10000 rpm for 20 min. The supernatant was stored at 4° C. (low-temperature storage). Samples were taken every 10 days. The enzyme activity of each sample was determined.

Comparative Example 3: The pH of the Enzyme Solution was not Adjusted in this Comparative Example After the fermentation of the engineered strain of D-psicose-3-epimerase was complete (i.e., the OD600 value of the fermentation broth no longer increases), aeration was stopped, and the lysozyme was added in an amount of 0.1 g/L (i.e., the concentration of the lysozyme in the fermentation broth is 0.1 g/L). The fermentation broth was stirred until the OD600 value of the fermentation broth is less than or equal to 1. The recombinant *Bacillus subtilis* engineered strain B-3-1 was dissolved to obtain an enzyme solution of D-psicose-3-epimerase. Then, the enzyme solution was stored at 30° C. Samples were taken every 10 days. The enzyme activity of each sample was determined. Table 1 shows the enzyme activities of Examples 1-7 and Comparative Examples 1-3.

TABLE 1

Enzyme activities of Examples 1-7 and Comparative Examples 1-3 (Unit: U/ml)

| | Day 0 | Day 10 | Day 20 | Day 30 | Day 40 | Day 50 | Day 60 |
|---|---|---|---|---|---|---|---|
| Example 1 | 424 | 420 | 415 | 412 | 409 | 402 | 398 |
| Example 2 | 424 | 418 | 410 | 403 | 397 | 391 | 386 |
| Example 3 | 424 | 422 | 419 | 418 | 414 | 410 | 404 |
| Example 4 | 424 | 416 | 407 | 398 | 391 | 382 | 375 |
| Example 5 | 424 | 419 | 412 | 405 | 400 | 390 | 387 |
| Example 6 | 424 | 415 | 407 | 399 | 391 | 384 | 379 |
| Example 7 | 424 | 414 | 406 | 398 | 393 | 388 | 381 |
| Comparative Example 1 | 424 | 424 | 420 | 415 | 413 | 410 | 408 |
| Comparative Example 2 | 424 | 401 | 384 | 372 | 360 | 348 | 330 |
| Comparative Example 3 | 424 | 406 | 389 | 375 | 366 | 353 | 341 |

It can be seen from Table 1 that after the fermentation broth was treated by a conventional scheme involving centrifugation and high-pressure homogenization (i.e., Comparative Example 2), the enzyme activity loss increases along with the storage time even if the fermentation broth was stored at a low temperature of 4° C. The enzyme activity was 330 on day 60, indicating a high enzyme activity loss of 22% or more. On day 15, the enzyme solution began to emit stinky odor, affecting the use of the enzyme solution. In addition, in Comparing Example 3, the enzyme activity was 341 on day 60, indicating an enzyme activity loss of 20%. The enzyme activity loss was high and the enzyme solution began to emit sour odor on day 20.

It can be seen by comparing Examples 1-7 and Comparative Example 1 of the invention that: compared with storage at 4° C., Comparative Example 1 required the use of freezers although the enzyme activity was high. In contrast, in Examples 1-7 of the invention, the enzyme solution did not emit stinky odor or sour odor after 60 days of storage at room temperature. Even when the storage temperature was 30° C., the enzyme solution still had good enzyme activity (91.0% of the initial enzyme activity) on day 60, indicating a low enzyme activity loss, and the enzyme solution had no stinky odor or sour odor. In addition, the enzyme activity determined in Examples 1-7 when the room temperature was 10° C. was basically the same as that determined in the case of storage at 4° C. This means that the preservation method of the invention can realize the storage of the enzyme solution at room temperature, does not require the use of freezers, and achieves a remarkable power-saving effect.

There was no strong stinky odor during storage in Examples 1-7 of the invention, indicating that the preservation method of the invention can avoid the growth of microorganisms in the enzyme solution even at room temperature, to ensure the enzyme activity and quality of the enzyme solution. In addition, it can be seen from Examples 1 to 7 that the enzyme activity obtained after storage using the preservation method of the invention for 60 days was 89.4% to 95.3% of the initial enzyme activity, indicating that the invention can realize the storage of the enzyme solution of D-psicose-3-epimerase at room temperature, can prevent the enzyme solution from emitting stinky odor or sour odor due to the growth of microorganisms during storage, and can ensure the enzyme activity.

The above examples are preferred embodiments of the invention, but the embodiments of the invention are not limited to thereto. Any other changes, modifications, replacements, combinations, and simplifications may be made without departing from the spirit and scope of the invention, which are all embraced in the scope of the invention.

What is claimed is:

1. A method for preserving a fermentation broth of an engineered strain of D-psicose-3-epimerase B-3-1, consisting of:

adding a lysozyme into a fermentation broth of an engineered strain of D-psicose-3-epimerase B-3-1, stirring to make the OD600 of the fermentation broth less than or equal to 1 to obtain an enzyme solution; and adjusting the enzyme solution to be weakly alkaline with a sodium hydroxide solution, and storing the weakly alkaline enzyme solution at room temperature, wherein the concentration of the lysozyme is 0.1 g/L, wherein in the step of adjusting the enzyme solution, the pH of the enzyme solution after the adjustment is 8.0, and wherein in the step of storing the weakly alkaline enzyme solution at room temperature, the room temperature is lower than or equal to 30° C.

* * * * *